United States Patent [19]
Stein et al.

[11] Patent Number: 5,949,846
[45] Date of Patent: Sep. 7, 1999

[54] BONE DENSITOMETRY USING X-RAY IMAGING SYSTEMS

[75] Inventors: Jay A. Stein, Framingham; Howard P. Weiss, Newton; Vincent E. Quinn, Bedford; Richard E. Cabral, Tewksbury; John A. Shepherd, Natick; Kevin E. Wilson, Cambridge, all of Mass.

[73] Assignee: Hologic, Inc., Waltham, Mass.

[21] Appl. No.: 08/794,615

[22] Filed: Feb. 3, 1997

[51] Int. Cl.⁶ .................................................. G01N 23/00
[52] U.S. Cl. ................................................ 378/54; 378/56
[58] Field of Search .................................. 378/54, 56, 57, 378/98.8, 98, 207, 208

[56] References Cited

U.S. PATENT DOCUMENTS

| | | |
|---|---|---|
| Re. 34,511 | 1/1994 | O'Neill et al. . |
| 3,639,764 | 2/1972 | Olson et al. ........................ 378/180 X |
| 4,029,963 | 6/1977 | Alvarez et al. . |
| 4,142,101 | 2/1979 | Yin . |
| 4,510,476 | 4/1985 | Clatterbuck et al. . |
| 4,517,472 | 5/1985 | Ruitberg et al. . |
| 4,774,959 | 10/1988 | Palmer et al. . |
| 4,789,930 | 12/1988 | Sones et al. ............................ 378/207 |
| 4,811,373 | 3/1989 | Stein . |
| 4,829,549 | 5/1989 | Vogel et al. .......................... 378/54 X |
| 4,947,414 | 8/1990 | Stein . |
| 4,953,189 | 8/1990 | Wang . |
| 5,040,199 | 8/1991 | Stein . |
| 5,134,999 | 8/1992 | Osipov . |
| 5,165,410 | 11/1992 | Warne . |
| 5,335,260 | 8/1994 | Arnold .................................. 378/56 X |
| 5,432,834 | 7/1995 | Gershman . |
| 5,483,960 | 1/1996 | Steiger et al. . |
| 5,506,880 | 4/1996 | Scardino et al. .................... 378/207 X |

*Primary Examiner*—David P. Porta
*Attorney, Agent, or Firm*—Cooper & Dunham LLP

[57] ABSTRACT

A method of measuring bone mineral density (BMD) of a selected region of bone in a small body portion (such as a limb or extremity), using a mini C-arm x-ray fluoroscopic imaging system to acquire the data from which the BMD is calculated. Apparatus for performing the method includes a tray for positioning the small body portion in the x-ray beam path of the imaging system and a sample of bone of predetermined density supported by the tray in side-by-side relation to the selected region of bone.

16 Claims, 7 Drawing Sheets

BONE DENSITOMETRY USING X-RAY IMAGING SYSTEMS

BACKGROUND OF THE INVENTION

1. Field of the Invention

This invention relates to methods of measuring bone mineral density (BMD) with x-ray fluoroscopic imaging equipment, and in particular to methods of measuring BMD in the limbs or extremities of a human or other animal with so-called mini C-arm x-ray fluoroscopic imaging systems, as well as to apparatus therefor.

2. Description of the Prior Art

In present-day medical practice, x-ray based systems are widely employed for bone densitometry (including measurement of BMD), e.g. to diagnose, evaluate and/or monitor osteoporosis. Apparatus and procedures for x-ray bone densitometry are described, for example, in U.S. Pat. Nos. 4,947,414 and 5,040,199, the complete disclosures of which are incorporated herein by this reference. X-ray bone densitometry has heretofore typically used a scanning pencil beam or fan beam of x-rays and a point detector or a linear array of point detectors, although the aforementioned U.S. Pat. No. 5,040,199 also describes use of a cone-shaped beam impinging on an x-ray image intensifier to produce an optical image that is viewed by a television camera. In general, known x-ray bone densitometers are dedicated systems of large weight and bulk that must be fixedly installed at permanent, stationary locations, occupying substantial area, although a system has been proposed that can fold so as to pass through a typical hospital room door. Pending U.S. patent application Ser. No. 08/484,568, filed Jun. 7, 1995 and assigned to the same assignee as the present application, describes and claims beam flattening in a fan-beam x-ray bone densitometer, and pending U.S. patent application Ser. No. 08/484,484, also filed Jun. 7, 1995, and assigned to the same assignee as the present application, describes and claims scanning sequences (with a fan beam) that include dual energy scans for BMD and single energy scans for imaging; both of these pending applications are incorporated herein by this reference.

As distinguished from densitometers, x-ray fluoroscopic imaging systems provide images of bone and tissue similar to conventional film x-ray shadowgrams but produced by conversion of an incident x-ray pattern to a "live" enhanced (intensified) optical image that can be displayed on a video monitor directly, i.e., essentially contemporaneously with the irradiation of the patient's body or body portion being imaged; the term "fluoroscopic imaging" is used herein to designate such provision of directly video-displayed x-ray images. In some x-ray fluoroscopic imaging systems, the entire system is carried on an easily movable cart and the x-ray source and detector are mounted on a rotatable mini C-arm dimensioned for examining smaller body parts such as the extremities (wrists, ankles, etc.) of a human patient. An imaging device, including an image intensifier, suitable for use in such a system is described in U.S. Pat. No. 4,142,101, the complete disclosure of which is incorporated herein by this reference; one illustrative example of a currently commercially available mini C-arm x-ray fluoroscopic imaging system is that currently sold under the trade name "FluoroScan III" by FluoroScan Imaging Systems, Inc., of Northbrook, Ill., a subsidiary of the assignee of the present application. Mini C-arm x-ray fluoroscopic imaging systems are economical in space, conveniently movable (as within a hospital, clinic or physician's office) to a desired temporary location of use, and offer superior safety (owing to low levels of electric current utilization and reduced exposure of personnel to scatter radiation) as well as ease of positioning the source and detector relative to a patient's extremity for imaging.

SUMMARY OF THE INVENTION

The present invention, in one aspect, contemplates the provision of a method of measuring BMD with an x-ray fluoroscopic imaging system that includes an x-ray source for emitting a volume x-ray beam (such as a cone beam or a pyramid beam, as opposed to pencil beams and fan beams) propagating along a beam path, a detector on which the beam impinges over a two-dimensional area representing a field of view, the detector being spaced from the source for enabling a bone-containing human or other animal body portion to be interposed therebetween in the path so as to be irradiated by the beam and generating output data representative thereof, the output data being a 2-dimensional electronic representation of the aforesaid area containing sufficient information for display on a video monitor as a visible representation of the image. As used with a system of this type, the method of the invention comprises the steps of interposing, between the source and the detector in the path of the beam, a human body portion containing bone having a selected region of which the BMD is to be measured and a sample of bone of predetermined BMD; operating the system, while the body portion and sample are thus positioned, to generate output data, representative of one or more images of the body portion bone and sample, sufficient for calculation of the BMD of the selected region of the body portion bone; correcting the output data thus obtained for inherent variations in each of two orthogonal directions of the output data over the field of view to produce corrected data; and deriving from the corrected data a value representative of the BMD of the selected region of the body portion bone.

The term "sample of bone of predetermined BMD" as used herein includes bone-equivalent material, e.g. synthetic material, for instance material of a type such as is currently used in some bone densitometry systems. In some instances an additional sample of calibration material such as tissue or tissue-equivalent material may also be interposed in the beam path.

In the method of the invention, the correcting step preferably comprises subtracting, from the initial output data, correction output data generated by the detector, representative of one or more 2-dimensional images produced by irradiating the field of view with the beam under conditions of known x-ray attenuation in the beam path. For instance, the correction output data may be generated under the condition that only air is present in the beam path between the source and the detector. In currently preferred embodiments of the method of the invention, however, the correction output data generated by the detector are representative of one or more 2-dimensional images produced by irradiating, with the beam, an object interposed between the source and the detector and having a known x-ray attenuation in the beam path in each of two orthogonal directions which are transverse to the beam path. Conveniently, this object may be a homogeneous object of uniform x-ray thickness in the beam path.

As a further feature of the invention, in currently preferred embodiments, the selected region of the body portion bone and the sample are disposed side by side within the beam path so as to be respectively represented by separate areas in an image displayed on a video monitor as aforesaid from the detector output data.

A preferred procedure for performing the step of operating the system to generate output data includes operating the system to generate first output data representative of at least one image of the body portion and sample produced while the source is emitting an x-ray beam at a first x-ray energy level (L) and second output data representative of at least a second image of the body portion and sample produced while the source is emitting an x-ray beam at a second x-ray energy level (H) higher than the first energy level (L). In these embodiments, the correction step preferably includes subtracting, from the first output data, first correction output data representative of at least one image of a known object interposed between the source and the detector, e.g. an object having uniform x-ray attenuation, produced while the source is emitting an x-ray beam at the first energy level (L) and subtracting, from the second output data, second correction output data representative of at least a second image of the same object interposed between the source and the detector produced while the source is emitting an x-ray beam at the second, higher energy level (H).

In at least some instances, it is advantageous to obtain the correction data each time the method is performed to measure the BMD of a bone in a body portion. The method in such cases thus includes the positive steps of operating the system, while the known object is interposed between the source and the detector x-ray, to generate the first correction output data and said second correction output data.

As a further feature of advantage and preference, the sample of bone of predetermined BMD may be a sample having plural portions disposed side-by-side in a plane transverse to the beam path and respectively having different predetermined thicknesses or other characteristics in a direction parallel to the beam path.

In certain embodiments of the invention, the detector may include an image intensifier, e.g. of a type for intensifying an optical image, or alternatively for intensifying an x-ray image.

Further, in such embodiments, where the image intensifier produces an optical image of objects interposed in the path and irradiated by the beam between the source and the detector, the detector also includes a video camera for viewing the produced image and generating output data representative thereof, the output data being generated in video format. As still another alternative, the detector may comprise a direct digital 2-dimensional x-ray detector, and in such case there is no video camera.

In a particularly advantageous aspect, the invention contemplates measuring bone mineral density (BMD) of a selected region of bone in a small body portion of a human or other animal by placing the small body portion in a mini C-arm x-ray fluoroscopic system to generate output data containing information sufficient for calculation of the BMD of the selected region of the body portion bone and deriving from the output data a value representative of the BMD of the selected region of the body portion bone.

Thereby, the invention overcomes various difficulties or inconveniences associated with conventional x-ray bone densitometers, such as the large space they require. With a mini C-arm x-ray fluoroscopic imaging system, BMD measurements can be readily made at a desired location, even in a physician's office which does not have a dedicated bone densitometer. Moreover, the method can be practiced using a currently commercially available mini C-arm x-ray fluoroscopic imaging system without affecting the capability of the system to be used for conventional fluoroscopic imaging as well, so that the system can function as a dual-purpose system.

In yet another aspect, the invention contemplates the provision of a system for measuring bone mineral density (BMD) of a selected region of bone in a small body portion of a human or other animal, comprising, in combination, an x-ray fluoroscopic imaging system as described above, including structure supporting the x-ray source and the detector in fixed relation to each other (which structure may be, in itself, a conventional type of support structure as heretofore so used in x-ray fluoroscopic imaging systems), and a tray, stably secured to the structure, having a guide surface shaped and disposed to locate and support a small body portion of a human patient in a predetermined position in the beam path between the source and the detector, the body portion containing bone having a selected region of which the BMD is to be measured, the tray further including a sample of bone of predetermined BMD, disposed laterally of the selected region of body portion bone with respect to the beam path so that the sample and the selected region are respectively represented by separate areas in an image displayed on a video monitor as aforesaid from the detector output data; and means for receiving output data from the detector representative of one or more images of the body portion bone and sample, sufficient for calculation of the BMD of the selected region of the body portion bone, and for correcting the output data for inherent 2-dimensional variations over the field of view and deriving from the corrected data a value representative of the BMD of the selected region of the body portion bone. In this apparatus, the sample of bone of predetermined BMD may be a sample having plural portions respectively having different predetermined x-ray thicknesses as described above.

Further features and advantages of the invention will be apparent from the detailed description hereinbelow set forth, together with the accompanying drawings.

DETAILED DESCRIPTION

The invention will be described, with reference to the drawings, as embodied in a method of measuring BMD of bones in the forearm or wrist, or in the ankle or heel (calcaneal region), of a human patient, using a mini C-arm x-ray fluoroscopic imaging system of the type exemplified by the currently commercially available "FluoroScan III" system mentioned above.

Figure 1:
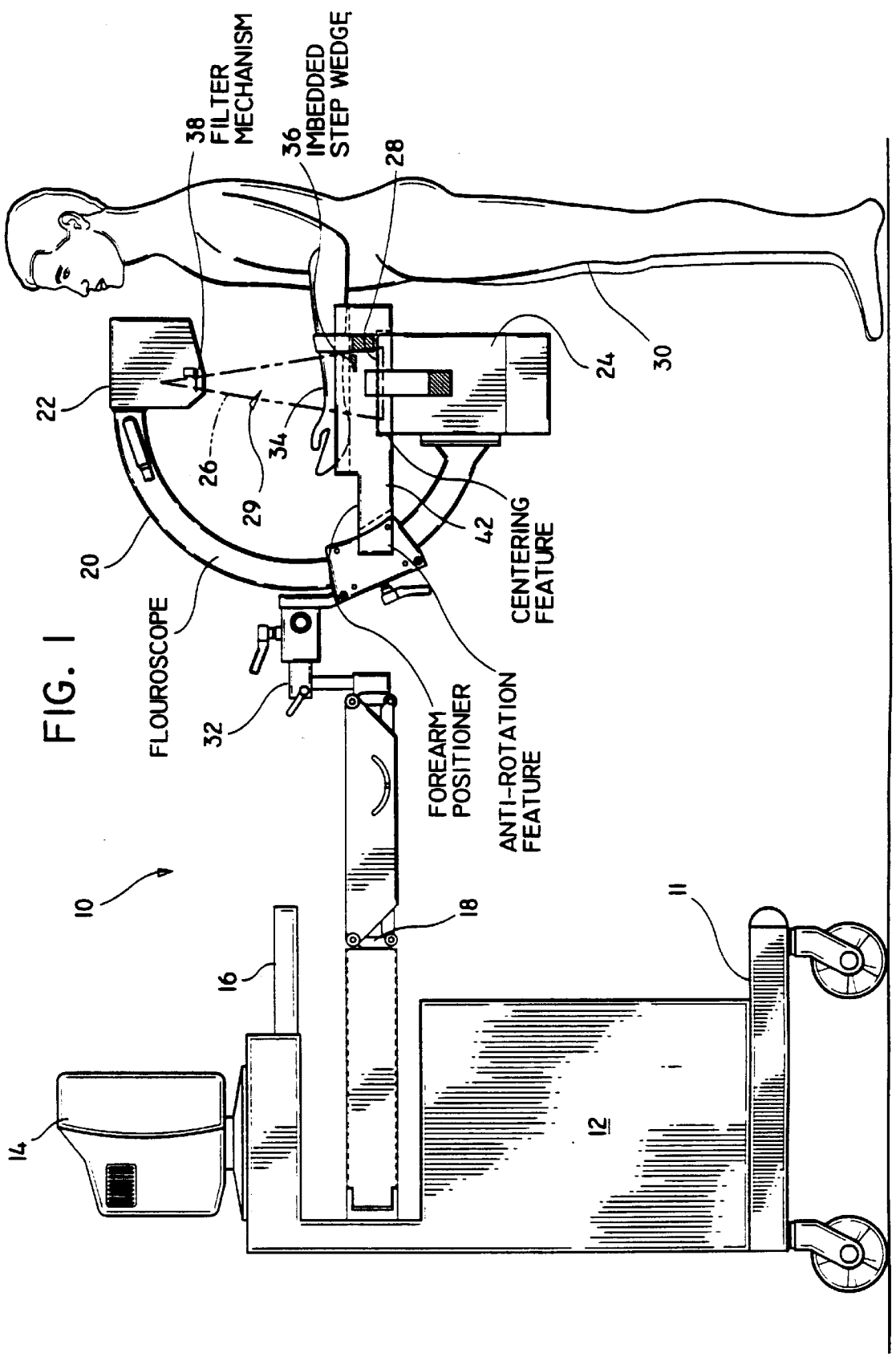
FIG. 1 is a simplified and partly schematic side elevational view of a mini C-arm x-ray fluoroscopic imaging system arranged for use to measure forearm BMD of a human patient, in an illustrative embodiment of the method of the present invention.

This imaging system, shown at 10 in FIG. 1, is entirely contained in a wheeled cart or cabinet 11 that can easily be rolled from place to place. The cabinet includes a generally rectangular, upright body 12 that supports dual video monitors 14 (only one being shown) on its top surface and has, in its upper portion, a keyboard 16 and an articulated member 18; the cabinet also contains a computer (not shown) for processing data as hereinafter further discussed. It will be understood that the present method can be practiced with use of only a single monitor, or indeed without a monitor (e.g., employing a printer to produce the BMD measurement data).

The outer end of articulated member 18 carries a mini C-arm 20 having an x-ray source 22 and a detector 24 respectively fixedly mounted at its opposite extremities so that an x-ray beam 26 from source 22 impinges on the input end 28 of the detector, the source and detector being spaced apart by the C-arm sufficiently to define a gap 29 between them, in which the limb or extremity of a human patient 30 can be inserted in the path of the x-ray beam 26. The C-arm is connected to the end of member 18 by a 3-way pivotal mounting 32 that enables the C-arm to be swivelled or rotated through 360° in each of three mutually perpendicular (x, y, z) planes and to be held stably at any desired position, while the member 18 is itself mounted and jointed to enable its outer end and the C-arm to be angularly displaced both horizontally and vertically. The multidirectional angular movability of the mini C-arm facilitates the positioning of the source and detector in relation to a patient body portion to be irradiated.

A suitable power supply for the x-ray source, and instrumentalities for controlling or varying current (mA) and voltage (kV), not shown, are incorporated in the system as well.

The beam 26 emitted by the x-ray source 22 is a cone-shaped beam (i.e. a volume beam as opposed to a pencil beam or fan beam) that impinges on a flat x-ray-sensitive receiving surface of the detector 24 at or adjacent the detector input end; this receiving surface faces the source across the gap 29 and is perpendicular to the axis of the beam path, so that the intersection of the receiving surface and the conical x-ray beam is an extended circular (2-dimensional) area. The term "field of view" is used herein to refer to the latter circular area, or that portion of it to which the detector responds, and also to designate the region, within the beam path or gap 29, the contents of which will be imaged by the detector. It will be understood that the area of the field of view as measured in a plane transverse to the beam path axis is sufficient to encompass objects of the size desired to be imaged or otherwise studied, e.g. a human wrist or heel.

The receiving surface of the detector 24 is a surface of an x-ray-to-visible-light converter, such as a layer of phosphor or scintillator material covered externally by a light shield, that converts impinging x-rays to visible light. The detector also includes an image intensifier of the high-gain microchannel plate type, and a planar output surface on which is produced an output visible-light image of the field of view, in accordance with well-known principles of fluoroscopic imaging. The combined converter and image intensifier elements of the detector 24 may be as described in the aforementioned U.S. Pat. No. 4,142,101.

In addition, the detector assembly includes a video camera (not separately shown) for viewing the image on the aforementioned planar output surface and producing a signal output representative of that viewed image. The video camera can be a television camera and can operate according to a video standard such as NTSC. When the system is employed for fluoroscopic imaging, the signal output of the video camera is processed by the onboard computer to produce video images on one or both monitors 14; the system also includes devices for recording and, optionally, printing out these video fluoroscopic images.

As thus far described, the system 10 is essentially identical to currently available mini C-arm x-ray fluoroscopic imaging systems. Thus, the system 10 may be a "FluoroScan III" system, having the following pertinent specifications:

OUTPUT FORMAT

Standard 2,200 Image Storage; Optional 4,000 Image Storage; Digital Video Output; Composite Video Output

VIDEO PROCESSING

Last Image Hold for 4 Images; Real Time Edge Enhancement; User Selectable Real Time Recursive Averaging; Noise Suppression; Automatic Contrast Enhancement; Automatic Brightness Control

INPUT POWER

110V~60 Hz Nominal; 90V~to 132V Actual; 47Hz to 63 Hz Actual; Non Dedicated, Grounded

WARM UP

3 Seconds

X-RAY POWER SUPPLY

Continuous Duty kV 40 kV to 75 kV in 2.15 kV Increments

ANODE CURRENT

20 $\mu$A to (0.020 mA) to 100 $\mu$A (0.1 mA) in 3.6 $\mu$A Increments

FOCAL SPOT

85 Micron (0.085 mm)

TUBE TYPE

Custom Designed Cold Anode

TUBE COOLING

Maximum Tube Temperature is 50° C. at Maximum Power After 4 Hours of Continuous Duty

TARGET

Tungsten

COLLIMATION

Fixed to Field of View Size

FIELDS OF VIEW 75 mm (3" Nominal)

100 mm (4" Nominal)

125 mm (5 " Nominal)

IMAGE INTENSIFIER

High Gain Micro Channel Plate with Minimum of 40,000 Gain

PIXEL ARRAY 768 pixels by 600 lines

DUAL VIDEO MONITORS

14" (36 cm) SVGA High Resolution Video Monitor Video Standard NTSC/VHS

OVERALL HEIGHT 53 inches

OVERALL FLOOR SPACE 4.7 ft$^2$ (25" wide by 27" deep)

In a currently preferred embodiment of the method of the invention for measuring the BMD of a selected region of interest in a bone of a small body portion (limb or extremity) of a patient, using the system shown in FIG. 1 and described above, the body portion (e.g. the wrist 34, as shown in FIGS. 1–5) is placed in the field of view within the gap 29 together with a calibration sample 36 of bone of known BMD, so that the image produced by the detector will include both the bone region of interest and the calibration sample. The system is operated to image the wrist 34 and sample 36 at a first, low x-ray energy level (L) and again at a second, high x-ray energy level (H), i.e., an x-ray energy level higher than (L). Image output signals from the television camera are digitized (by means of an A/D converter, not shown), converted to natural logarithms (lognat), and stored in a pixel array spatially corresponding to the visible image produced in the detector, e.g. at 8 bits/pixel. The edge enhancement feature of the imaging system is disabled.

As described in the aforementioned U.S. Pat. No. 4,947,414, with the use of low energy data and high energy data, BMD measurements can be calculated by a method based on dual-photon absorptiometry calculations. The latter patent refers to a function that may be written as $$F = \text{lognat } LEL - k \cdot \text{lognat } HEL \tag{1}$$

in which HEL and LEL are respectively the x-ray beam attenuation values at high energy level and low energy level exposures (after correction as described below), and k is the ratio of the attenuation coefficient of tissue at the low energy level to that at the high energy level. As will be apparent from the description herein, this calculation method is adaptable to the present invention, it being noted that (in contrast to the procedure described in the last-mentioned patent) there may be no separate tissue calibration, although the present invention in its broader aspects does not exclude the use and presence of tissue calibration material.

In order to provide a low energy level x-ray beam 26 and a high energy level x-ray beam 26 as necessary to perform imaging at each of the two levels, the output voltage of the power supply to the x-ray source 22 can be changed, for example between 40 kV (low energy level) and 70 kv (high energy level). Preferably, during high-energy-level imaging (but not during low-energy-level imaging) a filter 38, e.g. of copper or aluminum, is interposed in the x-ray beam between the source and the objects (wrist and calibration bone sample) being imaged during high-energy-level imaging, to enhance the energy separation between levels (it will be understood that the provision of this filter is in addition to any filtration that may be required by governmental authorities). Alternatively, insertion and removal of the filter alone (without change of the output voltage of the power supply) can be used to achieve an effective change in energy levels; as is known in the art, insertion of the filter in the x-ray beam raises the effective energy level, and removal of the filter lowers the effective energy level.

Preferably, in any given BMD measurement, the objects (wrist and calibration sample bone) in the field of view are repetitively imaged at each of the low and high energy levels. That is to say, with the objects located in the field-of-view region of the cone-shaped x-ray beam path in gap 29 and kept stationary relative to the x-ray source and the detector, x-rays from the source at the low energy level are passed through the objects to the detector, and typically 2, 4, 8 or 16 frames (or some other number of frames) of video image are taken by the TV camera at the low energy levels, processed (digitized, converted to natural logarithms) and combined either additively or by so-called recursive accumulation (recursive averaging) to obtain cumulative low-energy-level beam attenuation values for each pixel of the digitized low-energy-level composite image. This process is repeated at the high energy level to obtain cumulative high-energy-level beam attenuation values for each pixel of the digitized high-energy-level composite image. The values of kV and mA selected for each (low or high) energy level are held constant for all image acquisition steps at that level.

Since the detector in the fluoroscopic imaging system detects x-ray emission from a cone-beam source over an extended two-dimensional area (the cross-section of the x-ray beam path in the plane of the detector receiving surface), there is inherent variation (i.e., variation attributable to the source and/or the detector having the image intensifier, independent of attenuation by any object interposed in the beam path) in received radiation intensity over the field of view. The image data obtained for the wrist and calibration bone sample by the steps described above are corrected for this inherent variation in order to enable more accurate calculation of BMD.

In currently preferred embodiments of the invention, correction is provided by imaging a flat piece of material with the system at each of the same low and high energy levels (L) and (H) used in imaging the wrist and calibration bone. The flat piece of material is homogeneous in x-ray attenuation properties over the full extent of the field of view, and of uniform x-ray thickness (measured in a direction parallel to the axis of the beam path in gap 29) throughout, such x-ray thickness being preferably about equal to that of the object (wrist) which is the subject of the BMD determination. With no other object in the field of view, the flat piece of material is interposed in the beam path between the source and detector, its major surface planes being oriented perpendicular to the beam axis, and, by energizing the x-ray source sequentially at the low and the high x-ray energy levels, low energy level image data and high energy level image data are obtained and processed in the same manner as the data for the wrist and calibration bone, described above.

The low energy level image data (expressed as natural logarithms) for the flat piece of material (LEL correction output data) are subtracted from the low energy level data (in lognat form) for the wrist and calibration bone (LEL object output data), and similarly the high energy level image data for the flat piece of material (HEL correction output data) are subtracted from the high energy level data for the wrist and calibration bone (HEL object output data) to correct ("flatten") the object output data for nonuniformities in the x-ray beam or imaging chain. In this way, corrected (flattened) LEL and HEL image data are obtained.

In at least some instances, for superior accuracy, it may be desirable or preferable to perform the correction low and high energy level imaging steps (with the flat piece of material) for each given BMD measurement. Thus, the method (as applied to the wrist) in this illustrative embodiment involves the acquisition of four images (or sets of cumulative images), viz. 1) a low energy image of the wrist and calibration bone sample; 2) a high energy image of the same without repositioning; 3) a low energy image of the flat piece of material of approximately the same thickness; and 4) a high energy image of the same flat piece of material. These four images can be acquired in any sequence, e.g., 3, 4, 1, 2; 3, 4, 2, 1; 4, 3, 1, 2; etc. Preferably there is no movement between low energy and high energy images. In other cases, however, it may be sufficient to perform the correction imaging with the flat piece of material at intervals, for example once at the start of each day, and use the correction output data then obtained for each BMD measurement performed during the following interval (day).

Once the flattened LEL and HEL object image data have been obtained, by the procedure described above, the BMD calculation can be made. The data, as corrected lognat values, are stored on a pixel-by-pixel basis in a pixel matrix corresponding to the video image obtained by the TV camera from which the image data are derived and digitized. In a typical situation, the processed image includes not only the patient bone region for which the BMD measurement is to be calculated, but also other portions of the patient's wrist, with and without bone, the aforementioned calibration bone sample of known BMD, and areas of the field of view not occupied by either wrist or sample.

From the flattened low energy level and high energy level object image data, image regions are identified that represent wrist tissue without bone. Data for low and high level x-ray attenuation in the last-mentioned region of wrist tissue with no bone are used to calculate the relative attenuation of the low and high energy x-ray beams in tissue, i.e., to determine a value corresponding to k in formula (1) above. With this value, the digitized image data in lognat form and pixel matrix array are combined to produce a subtraction image; the measurements and calculations required to achieve a measurement of BMD of the selected bone region are then performed for particular image areas or groups of pixels of the subtraction image, viz., those representing the patient bone region of interest and the calibration bone sample, with the density of the patient bone finally determined by comparison to the calibration bone. The purpose of the calibration bone sample, and manner in which the calculations are made, will be apparent from the foregoing description in conjunction with that in the aforementioned U.S. Pat. No. 4,947,414.

Selection of the image regions (groups of pixels) to be used in the calculations may be done manually, or may be computer-aided or computer-performed, as known in the bone densitometry field.

It is at present preferred to locate the calibration bone sample of known BMD at a position, in the field of view, that is superposed on the patient body portion (wrist) being imaged but displaced to one side of the selected patient bone region as to which the BMD is to be determined. The calibration bone data obtained at such a position take into account the interaction of the patient's tissue with bone of known density. Alternatively, however, the calibration bone sample could be displaced laterally to one side of the entire body portion (but still within the field of view), or superposed on the bone region of interest (as in densitometry procedures described in U.S. Pat. No. 4,947,414) with appropriate modification of the formula used for calculation and/or in the number of HEL/LEL image sets required.

Figure 2:
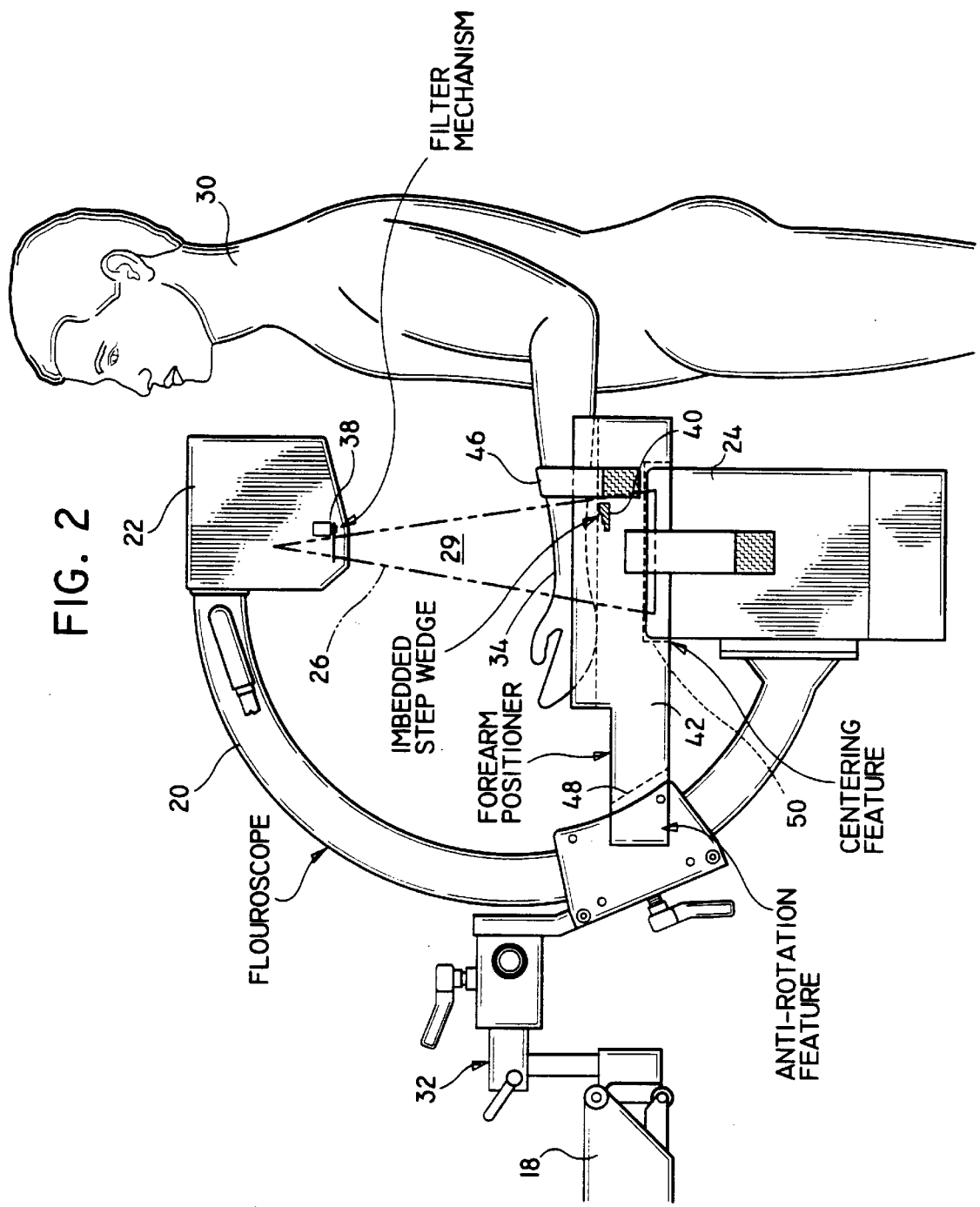
FIG. 2 is an enlarged view of a portion of FIG. 1.
Figure 3:
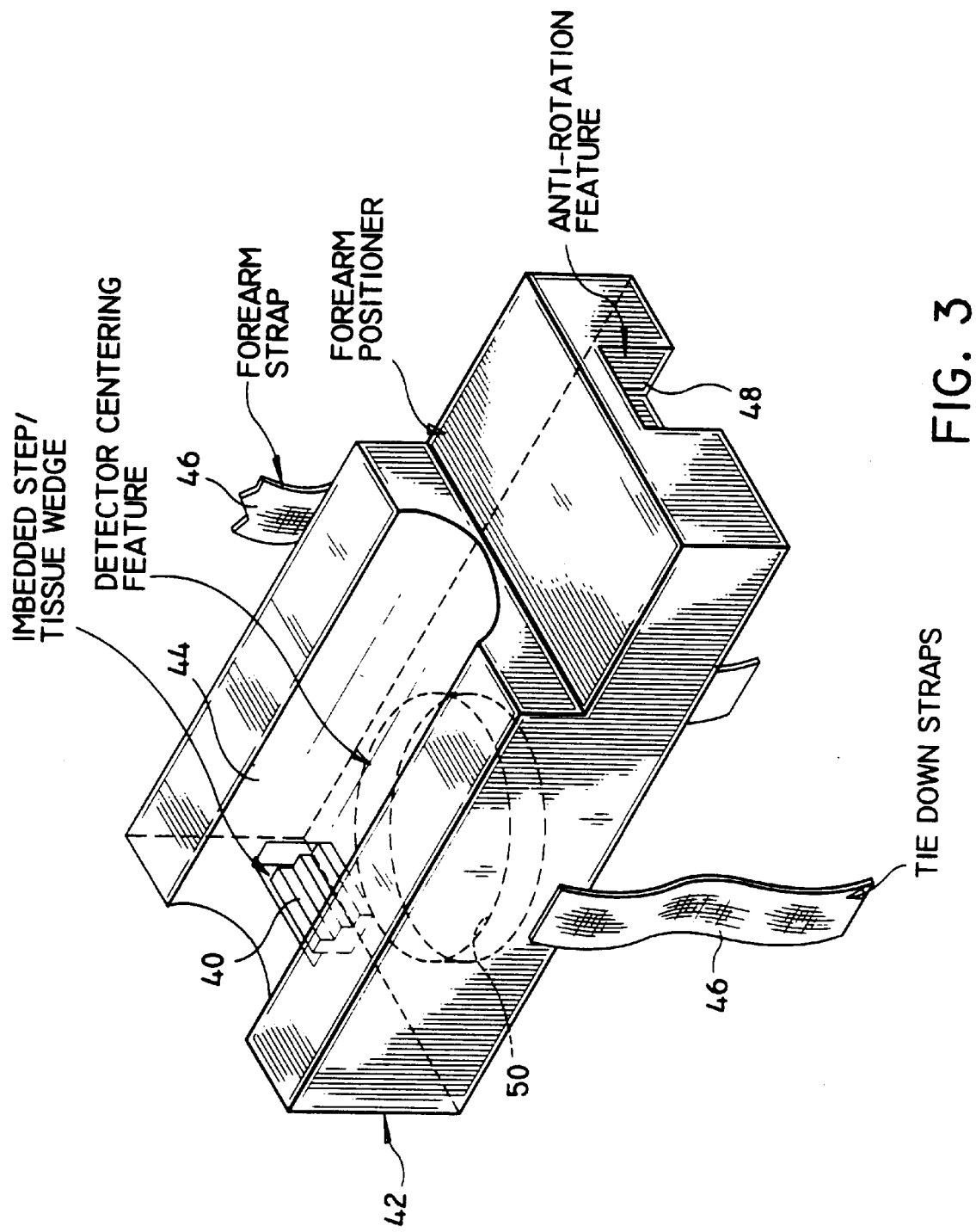
FIG. 3 is a further enlarged perspective view of a calibration/positioning fixture employed in the same system in the practice of the method of the invention as represented in FIG. 1 to measure forearm BMD.

Additionally, it is preferred that the calibration bone sample of known BMD be a sample having plural portions disposed side-by-side in a plane transverse to the beam path and respectively having different predetermined x-ray thicknesses in a direction parallel to the path, as shown at 40 in FIGS. 2 and 3. Such a stepped calibration sample facilitates calibration for patient bone regions of various different thicknesses. It will be understood that the calibration material may be a substance, other than actual bone, having similar characteristics to serve the calibration function; and that, in addition, a calibration sample for tissue may be included if desired.

As also best seen in FIGS. 2 and 3, and as a particular apparatus feature of the invention, a special accessory structure is provided for the imaging system to position the patient's arm and the calibration bone sample, which may be considered an element of this accessory structure. The structure is a rigid, substantially x-ray-transparent fixture 42 of horizontally elongated shape with a longitudinal trough 44 in its upper surface for guiding the patient's arm to and retaining the arm in a preselected fixed position during the imaging operation of the system 10. Straps 46 serve to hold the arm in place on the fixture. The calibration bone sample 40 is mounted in the trough, within but toward one side of the field of view. The feature 42 seats stably and securely on the C-arm 20 and the detector 24, and has recesses 48 and 50 formed in its lower surface for respectively receiving a portion of the C-arm and the upper end of the detector to insure that the fixture seats and remains in the proper position for imaging of the wrist.

Figure 4:
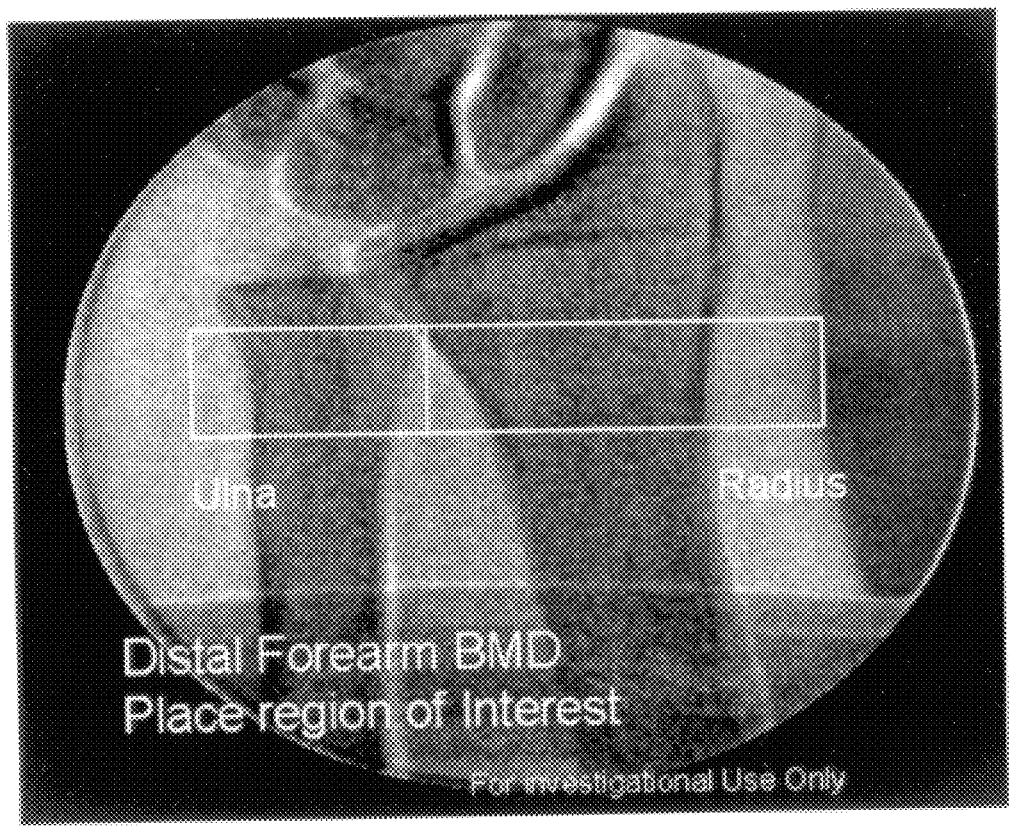
FIG. 4 is a sample of a distal forearm image such as would be displayed on one of dual video monitors of the same system in the practice of the method of the invention as represented in FIG. 1.
Figure 5:
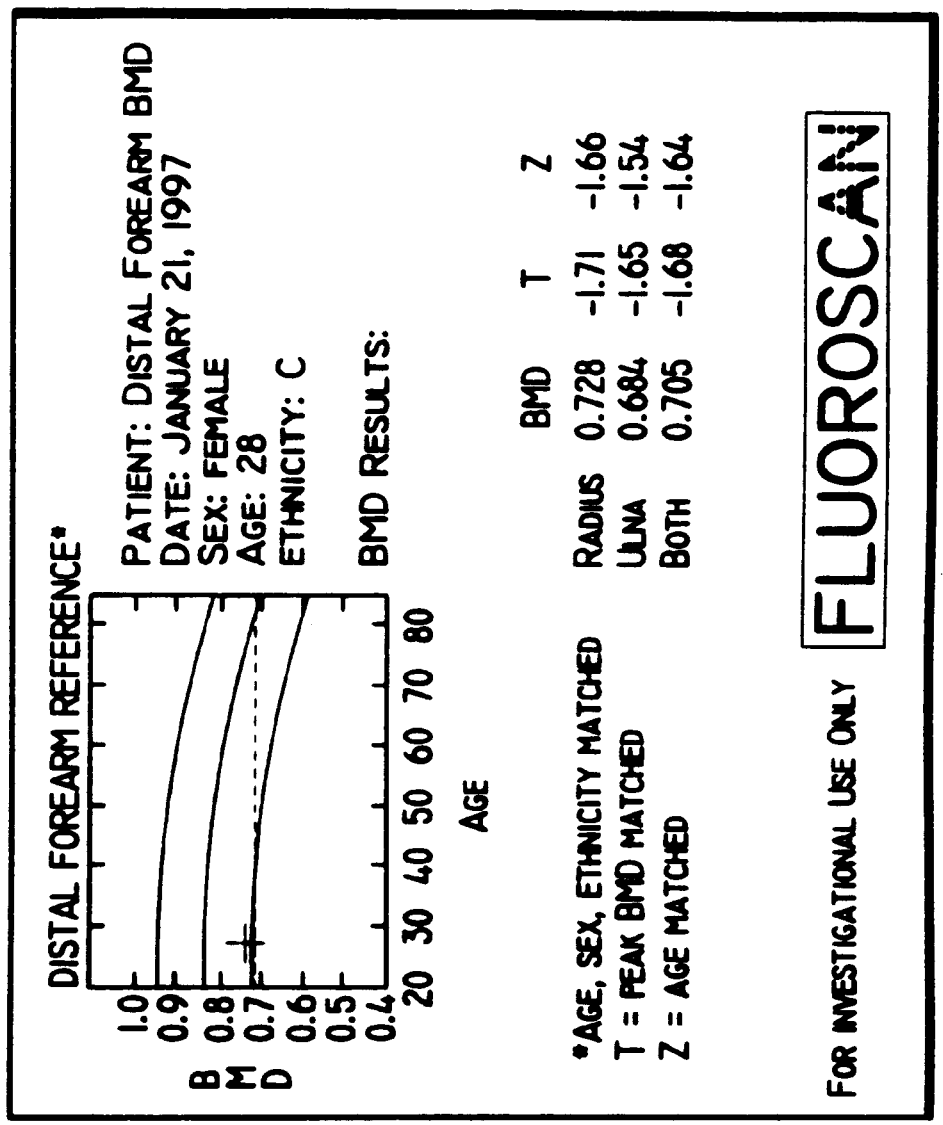
FIG. 5 is a sample of a forearm BMD data report such as would be displayed on the other of the dual video monitors of the same system in the practice of the method of the invention as represented in FIG. 1.

The two video monitors 14 of the imaging system 10 may be used, respectively, to display an image of the patient body portion indicating the bone region selected for BMD measurement, and a report of the BMD calculation and result provided by the method of the invention. FIG. 4 is a sample wrist image display, and FIG. 5 is a simulated display of a BMD report such as would be produced by the method of the invention.

Figure 6:
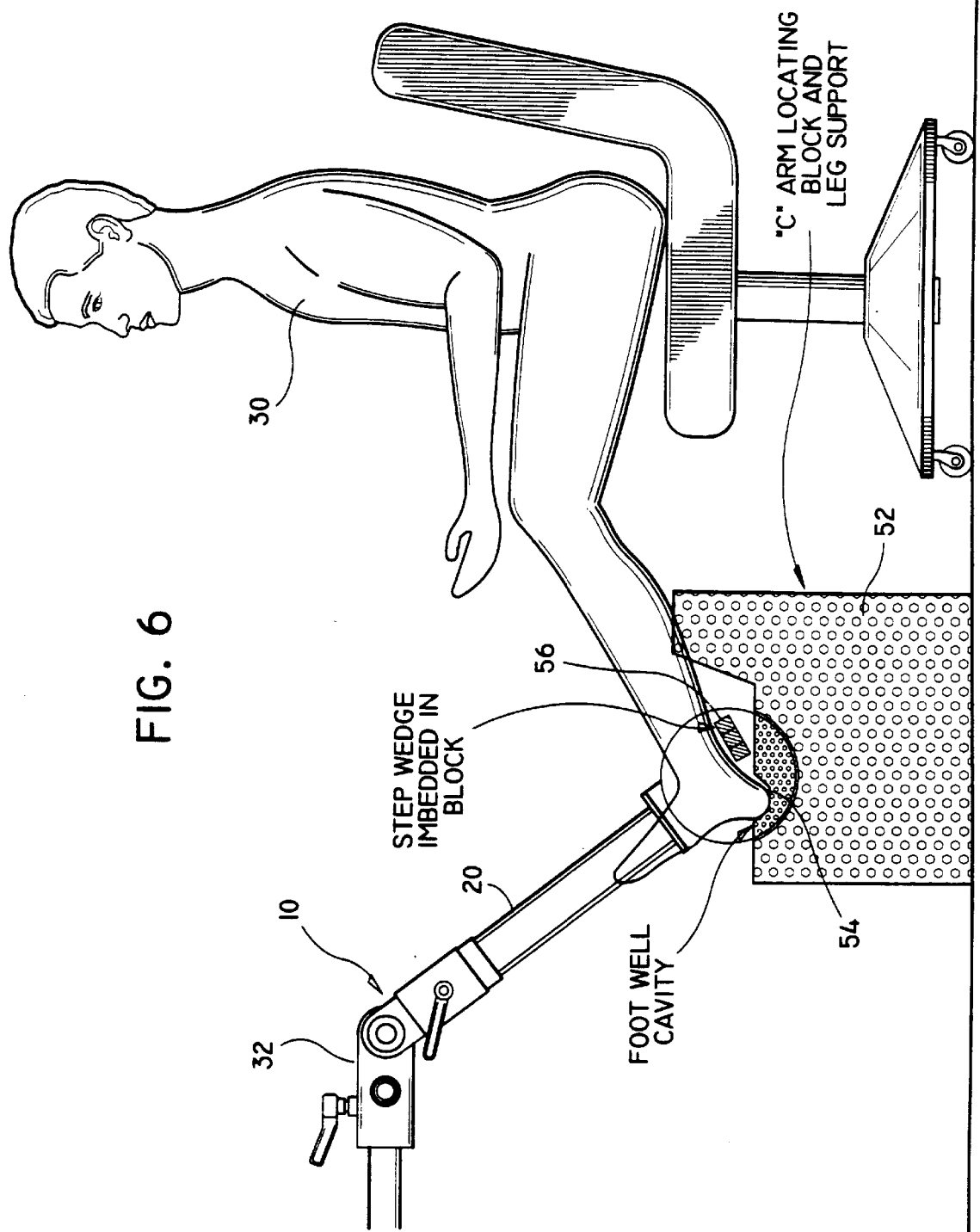
FIG. 6 is a view similar to FIG. 2 of the same system arranged for use to measure calcaneal BMD of a human patient, again in accordance with an embodiment of the present method.
Figure 7:
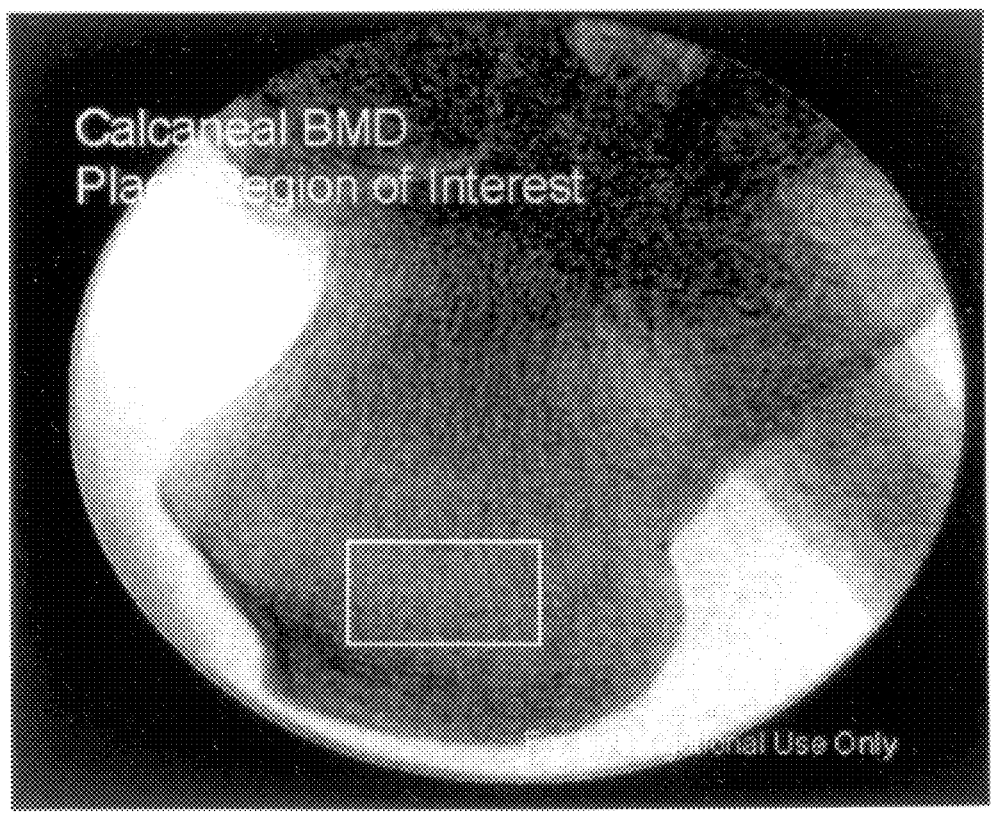
FIG. 7 is a sample of a calcaneal image such as would be displayed on one of dual video monitors of the same system in the practice of the method of the invention as represented in FIG. 7.

As an example of other patient body portions with which the method of the invention may be used to provide BMD measurements, reference may be made to FIG. 6, which shows the same imaging system 10 as in FIG. 1 arranged for measuring calcaneal BMD in a heel portion of a patient's lower extremity. The C-arm 20 has been rotated, for this procedure, so as to lie in a plane perpendicular to that of the drawing. Again in accordance with the invention, a fixture 52 in the form of a block having a heel-positioning recess 54 in its upper surface and a stepped calibrating bone sample 56 mounted within the field of view, so as to lie to one side of the heel when the heel in placed in the recess. A sample image of the heal, with the patient bone region of interest marked, is shown in FIG. 7.

While the measurement of BMD with the mini C-arm imaging system 10 is limited to thin objects (bones in small body portions, such as extremities) due to flux limitations inherent in the mini C-arm system, the invention in its broader aspects embraces the use of systems providing greater x-ray flux, with area detectors incorporating image intensifiers, to perform such measurements e.g. on larger bones and/or larger body portions, such as the axial skeleton. Conversely, the invention may be practiced with fully portable, battery-powered C-arm fluoroscopic imaging systems such as can be carried and used in the field.

As stated, in its above-described embodiments, the method of the invention calculates BMD in a manner based on dual-photon absorptiometry, which involves the acquisition of images at two different energy levels. With an alternative calculation procedure, based on so-called single-photon absorptiometry, only single-energy imaging is used. Single energy densitometry requires including bolus material (such as a water bag) in the scanned field to equalize the x-ray thickness of the scanned object across the field of view.

Further alternatives to or modifications of the embodiments described above include scanning calibration materials separately to obtain either the relative attenuation of the low and high energy x-ray beams and/or the value of the calibration bone. This alternative is possible with an imaging system used having a stable x-ray source and a linear x-ray detection system not available in current mini C-arm fluoroscopic imaging systems. An additional alternative or modification is to calculating body composition (fat vs. lean mass) for tissue points in the scanned region.

A wide variety of additional alternatives are embraced within the scope of the invention in its broader aspects. For instance, the image intensifier employed in the detector may be either of a type that intensifies optical images (as in the above-described "FluoroScan III" system) or of a type that intensifies x-ray images. Again, in place of an image intensifier and video camera, the detector may be a direct digital 2-dimensional x-ray detector; an example of such a device is the "FlashScan 20" high resolution flat panel device of dpiX, A Xerox Company, which is an amorphous silicon image sensor that acquires conventional x-ray images and converts them to digital form in a way that can provide fluoroscopic imaging in real time.

The calculation of data to produce BMD measurements could be performed with an onboard computer in a mini C-arm fluoroscopic system such as the "FluoroScan III" system, or in another computer. The functions of data acquisition/storage and BMD computation therefrom could be performed by different computers. Also, instead of digitizing the detector output data before conversion to logarithms, the logarithmic conversion could be performed first (e.g. with a log amplifier) and digitized thereafter. Moreover, in addition to or in place of the fixtures described above for holding the body portion stationary, appropriate software could be employed to reregister the images if there is movement.

It is to be understood that the invention is not limited to the procedures and embodiments hereinabove specifically set forth, but may be carried out in other ways without departure from its spirit.

What is claimed is:

1. A method of measuring bone mineral density (BMD) with an x-ray fluoroscopic imaging system that includes an x-ray source for emitting a volume x-ray beam propagating along a beam path, a detector on which the beam impinges over a two-dimensional area, the detector being spaced from the source for enabling a bone-containing human or other animal body portion to be interposed therebetween in the path so as to be irradiated by the beam and generating output data representative thereof, said output data being a 2-dimensional electronic representation of said area containing sufficient information for display on a video monitor as a visible representation of an image of objects interposed in the path, said method comprising the steps of:

(a) interposing, between the source and the detector in the path of the beam, a human body portion containing bone having a selected region of which the BMD is to be measured and a sample of bone of predetermined BMD;

(b) operating the system, while the body portion and sample are interposed as aforesaid, to generate output data, representative of one or more images of said body portion bone and sample, sufficient for calculation of the BMD of the selected region of the body portion bone;

(c) correcting the output data obtained in step (b) for inherent variations in each of two orthogonal directions of said output data over said area to produce corrected data; and (d) deriving from the corrected data a value representative of the BMD of the selected region of the body portion bone.

2. A method according to claim 1, wherein step (c) comprises subtracting, from the output data obtained in step (b), output data representative of one or more images produced by irradiating, with the beam, an object interposed between the source and the detector and having known x-ray attenuation in each of two orthogonal directions which are transverse to the beam path.

3. A method according to claim 2, wherein said object is a homogeneous object of uniform x-ray thickness in said path.

4. A method according to claim 1, wherein the selected region of the body portion bone and the sample are disposed side by side within the beam path during step (b) so as to be respectively represented by separate areas in an image displayed on a video monitor as aforesaid.

5. A method according to claim 4, wherein step (b) includes operating the system to generate first output data representative of at least one image of the body portion and sample produced while the source is emitting an x-ray beam at a first x-ray energy level (L) and second output data representative of at least a second image of the body portion and sample produced while the source is emitting an x-ray beam at a second x-ray energy level (H) higher than said first x-ray energy level (L).

6. A method according to claim 5, wherein step (c) includes subtracting, from said first output data, first correction output data representative of at least one image of an object interposed between the source and the detector and having known x-ray attenuation in each of two orthogonal directions which are transverse to the beam path, produced while the source is emitting an x-ray beam at a first energy level (L) and subtracting, from said second output data, second correction output data representative of at least a second image of said object interposed between the source and the detector, produced while the source is emitting an x-ray beam at a second energy level (H) higher than said first energy level (L).

7. A method according to claim 6, wherein step (c) includes the steps of operating the system, while said object is interposed between the source and the detector, to generate said first correction output data and said second correction output data.

8. A method according to claim 7, wherein said object is a homogeneous object of uniform x-ray thickness in said path.

9. A method according to claim 1, wherein said sample of bone of predetermined BMD is a sample having plural portions disposed side-by-side in a plane transverse to said path and respectively having different predetermined x-ray thicknesses in a direction parallel to said path.

10. A method according to claim 1, wherein said detector includes an image intensifier for intensifying an optical image.

11. A method according to claim 10, wherein said image intensifier produces an optical image of objects interposed in the path and irradiated by the beam between the source and the detector, and wherein said detector further includes a video camera for viewing the produced image and generating output data representative thereof, said output data being generated in video format.

12. A method according to claim 1, wherein said detector includes an image intensifier for intensifying an x-ray image.

13. A method according to claim 1, wherein said detector comprises a direct digital 2-dimensional x-ray detector.

14. A method of measuring bone mineral density (BMD) of a selected region of bone in a small body portion of a human patient, comprising (a) imaging the small body portion in a mini C-arm x-ray fluoroscopic imaging system to generate output data in video format containing information sufficient for calculation of the BMD of the selected region of the body portion bone and (b) deriving from the output data a value representative of the BMD of the selected region of the body portion bone.

15. A system for measuring bone mineral density (BMD) of a selected region of bone in a small body portion of a human or other animal, comprising, in combination,
 (a) an x-ray fluoroscopic imaging system including
  (i) an x-ray source for emitting a volume x-ray beam propagating along a beam path,
  (ii) a detector on which the beam impinges over a two-dimensional area, the detector being spaced from the source for enabling a bone-containing human or other animal small body portion to be interposed therebetween in the path so as to be irradiated by the beam, and generating output data representative thereof, said output data being a 2-dimensional electronic representation of said area containing sufficient information for display on a video monitor as a visible representation of an image of objects interposed in said path, and
  (iii) structure supporting said source and said detector in fixed relation to each other;
 (b) a tray, stably secured to said structure, having a guide surface shaped and disposed to locate and support a small body portion of a human patient in a predetermined position in said beam path between said source and said detector, said body portion containing bone having a selected region of which the BMD is to be measured, said tray further including a sample of bone of predetermined BMD, disposed laterally of said selected region of bone with respect to said beam path so that said sample and said selected region are respectively represented by separate areas in an image produced on a video monitor as aforesaid from said output data; and
 (c) means for receiving output data from said detector representative of one or more images of said body portion bone and sample, sufficient for calculation of the BMD of the selected region of the body portion bone, and for correcting said output data for inherent spatial variations in each of two orthogonal directions over said area and deriving from the corrected data a value representative of the BMD of the selected region of the body portion bone.

16. Apparatus as defined in claim 15, wherein said sample of bone of predetermined BMD is a sample having plural portions disposed side-by-side in a plane transverse to said path and respectively having different predetermined x-ray thicknesses in a direction parallel to said path.

* * * * *

UNITED STATES PATENT AND TRADEMARK OFFICE
Certificate

Patent No. 5,949,846

Patented: September 7, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jay A. Stein, Framingham, Ma.; Howard P. Weiss, Newton, Ma.; Vincent E. Quinn, Bedford, Ma.; Richard E. Cabral, Tewksbury, Ma.; John A. Shepherd, Natick, Ma.; Kevin E. Wilson, Cambridge, Ma.; and Joel Weinstein, Framingham, Ma.

Signed and Sealed this Thirteenth Day of November, 2001.

DONALD T. HAJEC
Supervisory Patent Examiner
Art Unit 2876